United States Patent
Sanchez et al.

(10) Patent No.: US 9,981,096 B2
(45) Date of Patent: May 29, 2018

(54) METHODS AND SYSTEMS FOR TRIGGERING WITH UNKNOWN INSPIRATORY FLOW

(71) Applicant: Covidien LP, Boulder, CO (US)

(72) Inventors: Gabriel Sanchez, Valley Center, CA (US); Nancy F. Dong, Carlsbad, CA (US)

(73) Assignee: Covidien LP, Mansfield, MA (US)

(*) Notice: Subject to any disclaimer, the term of this patent is extended or adjusted under 35 U.S.C. 154(b) by 680 days.

(21) Appl. No.: 13/798,949

(22) Filed: Mar. 13, 2013

(65) Prior Publication Data

US 2014/0261410 A1 Sep. 18, 2014

(51) Int. Cl.
*A61M 16/00* (2006.01)

(52) U.S. Cl.
CPC ..... *A61M 16/0051* (2013.01); *A61M 16/0063* (2014.02); *A61M 2016/0021* (2013.01); *A61M 2016/0027* (2013.01); *A61M 2016/0039* (2013.01); *A61M 2016/0042* (2013.01); *A61M 2202/0208* (2013.01); *A61M 2205/502* (2013.01)

(58) Field of Classification Search
CPC .......... A61M 16/0051; A61M 16/0063; A61M 16/204; A61M 2016/0042; A61M 2016/0039; A61M 2016/0021; A61M 2205/17; A61M 16/205; A61M 2016/0027
USPC ....................................... 128/202.22, 204.23
See application file for complete search history.

(56) References Cited

U.S. PATENT DOCUMENTS

| | | | |
|---|---|---|---|
| 3,584,621 A | 6/1971 | Bird et al. | |
| 3,586,021 A | 6/1971 | McGuinness | |
| 3,633,576 A | 1/1972 | Gorsuch | |
| 3,662,751 A | 5/1972 | Barkalow et al. | |
| 3,664,370 A | 5/1972 | Warnow | |
| 3,669,108 A | 6/1972 | Sundblom et al. | |
| 3,695,263 A | 10/1972 | Kipling | |
| 3,741,208 A | 6/1973 | Jonsson et al. | |
| 3,753,436 A | 8/1973 | Bird et al. | |
| 3,756,229 A | 9/1973 | Ollivier | |
| 3,768,468 A | 10/1973 | Cox | |
| 3,789,837 A | 2/1974 | Philips et al. | |
| 3,827,433 A | 8/1974 | Shannon | |
| 3,834,382 A | 9/1974 | Lederman et al. | |
| 3,869,771 A | 3/1975 | Bollinger | |
| 3,889,669 A | 6/1975 | Weigl | |
| 3,889,670 A | 6/1975 | Loveland et al. | |

(Continued)

FOREIGN PATENT DOCUMENTS

WO 2003055552 7/2003

OTHER PUBLICATIONS

7200 Series Ventilator, Options, and Accessories: Operators Manual. Nellcor Puritan Bennett, Part No. 22300 A, Sep. 1990, pp. 1-196.

(Continued)

*Primary Examiner* — Tan-Uyen (Jackie) T Ho
*Assistant Examiner* — Margaret Luarca

(57) ABSTRACT

This disclosure describes systems and methods for providing novel back-up ventilation that allows the patient to trigger or initiate the delivery of breath. Further, this disclosure describes systems and methods for triggering ventilation when base flow and/or inspiratory flow is unknown or indeterminable by the ventilator.

10 Claims, 6 Drawing Sheets

(56) References Cited

U.S. PATENT DOCUMENTS

| | | |
|---|---|---|
| 3,896,800 A | 7/1975 | Cibulka |
| 3,903,881 A | 9/1975 | Weigl |
| 3,905,362 A | 9/1975 | Eyrick et al. |
| 3,908,987 A | 9/1975 | Boehringer |
| 3,910,261 A | 10/1975 | Ragsdale et al. |
| 3,923,056 A | 12/1975 | Bingmann et al. |
| 3,961,627 A | 6/1976 | Ernst et al. |
| 3,976,052 A | 8/1976 | Junginger et al. |
| 3,976,065 A | 8/1976 | Durkan |
| 3,981,301 A | 9/1976 | Warnow et al. |
| 4,003,377 A | 1/1977 | Dahl |
| 4,020,834 A | 5/1977 | Bird |
| 4,029,120 A | 6/1977 | Christianson |
| 4,044,763 A | 8/1977 | Bird |
| 4,050,458 A | 9/1977 | Friend |
| 4,057,059 A | 11/1977 | Reid, Jr. et al. |
| 4,060,078 A | 11/1977 | Bird |
| 4,082,093 A | 4/1978 | Fry et al. |
| 4,121,578 A | 10/1978 | Torzala |
| 4,155,357 A | 5/1979 | Dahl |
| 4,164,219 A | 8/1979 | Bird |
| 4,197,843 A | 4/1980 | Bird |
| 4,197,856 A | 4/1980 | Northrop |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,245,633 A | 1/1981 | Erceg |
| 4,265,237 A | 5/1981 | Schwanbom et al. |
| 4,267,827 A | 5/1981 | Racher et al. |
| 4,275,722 A | 6/1981 | Sorensen |
| 4,281,651 A | 8/1981 | Cox |
| 4,285,340 A | 8/1981 | Gezari et al. |
| 4,320,754 A | 3/1982 | Watson et al. |
| 4,323,064 A | 4/1982 | Hoenig et al. |
| 4,340,044 A | 7/1982 | Levy et al. |
| 4,351,328 A | 9/1982 | Bodai |
| 4,351,329 A | 9/1982 | Ellestad et al. |
| 4,351,344 A | 9/1982 | Stenzler |
| 4,401,115 A | 8/1983 | Monnier |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,596,246 A | 6/1986 | Lyall |
| 4,598,706 A | 7/1986 | Darowski et al. |
| 4,611,591 A | 9/1986 | Inui et al. |
| 4,612,928 A | 9/1986 | Tiep et al. |
| 4,622,976 A | 11/1986 | Timpe et al. |
| 4,640,277 A | 2/1987 | Meyer et al. |
| 4,648,407 A | 3/1987 | Sackner |
| 4,651,731 A | 3/1987 | Vicenzi et al. |
| 4,752,089 A | 6/1988 | Carter |
| 4,757,824 A | 7/1988 | Chaumet |
| 4,766,894 A | 8/1988 | Legrand et al. |
| 4,796,618 A | 1/1989 | Garraffa |
| 4,813,409 A | 3/1989 | Ismach |
| 4,821,709 A | 4/1989 | Jensen |
| 4,877,023 A | 10/1989 | Zalkin |
| 4,889,116 A | 12/1989 | Taube |
| 4,921,642 A | 5/1990 | LaTorraca |
| 4,924,862 A | 5/1990 | Levinson |
| 4,954,799 A | 9/1990 | Kumar |
| 4,981,295 A | 1/1991 | Belman et al. |
| 4,982,735 A | 1/1991 | Yagata et al. |
| 5,002,050 A | 3/1991 | McGinnis |
| 5,007,420 A | 4/1991 | Bird |
| 5,016,626 A | 5/1991 | Jones |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,737 A | 12/1991 | Goulding |
| 5,099,837 A | 3/1992 | Russel, Sr. et al. |
| 5,150,291 A | 9/1992 | Cummings et al. |
| 5,154,167 A | 10/1992 | Hepburn |
| 5,158,569 A | 10/1992 | Strickland et al. |
| 5,161,525 A | 11/1992 | Kimm et al. |
| 5,165,397 A | 11/1992 | Arp |
| 5,165,398 A | 11/1992 | Bird |
| 5,222,491 A | 6/1993 | Thomas |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,698 A | 4/1994 | Tobia et al. |
| 5,315,989 A | 5/1994 | Tobia |
| 5,316,009 A | 5/1994 | Yamada |
| 5,318,487 A | 6/1994 | Golen et al. |
| 5,319,540 A | 6/1994 | Lsaza et al. |
| 5,323,772 A | 6/1994 | Linden et al. |
| 5,325,861 A | 7/1994 | Goulding |
| 5,333,606 A | 8/1994 | Schneider et al. |
| 5,335,651 A | 8/1994 | Foster et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,458,137 A | 10/1995 | Axe et al. |
| 5,479,920 A | 1/1996 | Piper et al. |
| 5,487,383 A | 1/1996 | Levinson |
| 5,494,028 A | 2/1996 | DeVries et al. |
| 5,507,282 A | 4/1996 | Younes |
| 5,509,406 A | 4/1996 | Kock et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,549,655 A | 8/1996 | Erickson |
| 5,551,419 A | 9/1996 | Froehlich et al. |
| 5,564,416 A | 10/1996 | Jones |
| 5,575,283 A | 11/1996 | Sjoestrand |
| 5,582,163 A | 12/1996 | Bonassa |
| 5,596,984 A | 1/1997 | O'Mahoney et al. |
| 5,603,315 A | 2/1997 | Sasso, Jr. |
| 5,606,968 A | 3/1997 | Mang |
| 5,615,669 A | 4/1997 | Olsson et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,645,053 A | 7/1997 | Remmers et al. |

(56) References Cited

U.S. PATENT DOCUMENTS

| | | |
|---|---|---|
| 5,647,345 A | 7/1997 | Saul |
| 5,647,351 A | 7/1997 | Weismann et al. |
| 5,651,360 A | 7/1997 | Tobia |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,694,926 A * | 12/1997 | DeVries et al. ......... 128/205.24 |
| 5,706,799 A | 1/1998 | Imai et al. |
| 5,715,812 A | 2/1998 | Deighan et al. |
| 5,720,277 A | 2/1998 | Olsson et al. |
| 5,727,562 A | 3/1998 | Beck |
| 5,730,122 A | 3/1998 | Lurie |
| 5,735,267 A | 4/1998 | Tobia |
| 5,738,090 A | 4/1998 | Lachmann et al. |
| 5,740,796 A | 4/1998 | Skog |
| 5,752,509 A | 5/1998 | Lachmann et al. |
| 5,762,480 A | 6/1998 | Adahan |
| 5,769,072 A | 6/1998 | Olsson et al. |
| 5,771,884 A | 6/1998 | Yarnell et al. |
| 5,791,339 A | 8/1998 | Winter |
| 5,794,615 A | 8/1998 | Estes |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,868,133 A | 2/1999 | DeVries et al. |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,162 A | 8/1999 | Christian |
| 5,934,274 A | 8/1999 | Merrick et al. |
| 5,970,975 A | 10/1999 | Estes et al. |
| 5,975,081 A | 11/1999 | Hood et al. |
| 5,983,891 A | 11/1999 | Fukunaga |
| 6,000,396 A | 12/1999 | Melker et al. |
| 6,003,513 A | 12/1999 | Readey et al. |
| 6,010,459 A | 1/2000 | Silkoff et al. |
| 6,024,089 A | 2/2000 | Wallace et al. |
| 6,029,664 A | 2/2000 | Zdrojkowski et al. |
| 6,029,667 A | 2/2000 | Lurie |
| 6,041,780 A | 3/2000 | Richard et al. |
| 6,042,550 A | 3/2000 | Haryadi et al. |
| 6,044,841 A | 4/2000 | Verdun et al. |
| 6,047,860 A | 4/2000 | Sanders |
| 6,066,101 A | 5/2000 | Johnson et al. |
| 6,067,984 A | 5/2000 | Piper |
| 6,076,519 A | 6/2000 | Johnson |
| 6,076,523 A | 6/2000 | Jones et al. |
| 6,095,139 A | 8/2000 | Psaros |
| 6,095,140 A | 8/2000 | Poon et al. |
| 6,102,038 A | 8/2000 | DeVries |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,674 A | 9/2000 | Rich |
| 6,135,106 A | 10/2000 | Dirks et al. |
| 6,138,675 A | 10/2000 | Berthon-Jones |
| 6,142,150 A | 11/2000 | O'Mahoney |
| 6,148,814 A | 11/2000 | Clemmer et al. |
| 6,152,132 A | 11/2000 | Psaros |
| 6,158,432 A | 12/2000 | Biondi et al. |
| 6,158,433 A | 12/2000 | Ong et al. |
| 6,161,539 A | 12/2000 | Winter |
| 6,192,885 B1 | 2/2001 | Jalde |
| 6,200,271 B1 | 3/2001 | Kuck et al. |
| 6,210,342 B1 | 4/2001 | Kuck et al. |
| 6,213,119 B1 | 4/2001 | Brydon et al. |
| 6,217,524 B1 | 4/2001 | Orr et al. |
| 6,220,244 B1 | 4/2001 | McLaughlin |
| 6,220,245 B1 | 4/2001 | Takabayashi et al. |
| 6,230,708 B1 | 5/2001 | Radko |
| 6,238,351 B1 | 5/2001 | Orr et al. |
| 6,241,681 B1 | 6/2001 | Haryadi et al. |
| 6,258,038 B1 | 7/2001 | Haryadi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,305,374 B1 | 10/2001 | Zdrojkowski et al. |
| 6,306,098 B1 | 10/2001 | Orr et al. |
| 6,318,365 B1 | 11/2001 | Vogele et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,427,692 B1 | 8/2002 | Hoglund |
| 6,439,229 B1 | 8/2002 | Du et al. |
| 6,443,154 B1 | 9/2002 | Jalde et al. |
| 6,450,163 B1 | 9/2002 | Blacker et al. |
| 6,450,968 B1 | 9/2002 | Wallen et al. |
| 6,467,477 B1 | 10/2002 | Frank et al. |
| 6,467,478 B1 | 10/2002 | Merrick et al. |
| 6,510,846 B1 | 1/2003 | O'Rourke |
| 6,512,938 B2 | 1/2003 | Claure et al. |
| 6,526,970 B2 | 3/2003 | DeVries et al. |
| 6,532,957 B2 | 3/2003 | Berthon-Jones |
| 6,532,960 B1 | 3/2003 | Yurko |
| 6,537,228 B1 | 3/2003 | Lambert |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,557,553 B1 | 5/2003 | Borrello |
| 6,560,991 B1 | 5/2003 | Kotliar |
| 6,564,798 B1 | 5/2003 | Jalde |
| 6,568,387 B2 | 5/2003 | Davenport et al. |
| 6,571,795 B2 | 6/2003 | Bourdon |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,595,212 B1 | 7/2003 | Arnott |
| 6,601,583 B2 | 8/2003 | Pessala et al. |
| 6,609,517 B1 | 8/2003 | Estes et al. |
| 6,622,725 B1 | 9/2003 | Fisher et al. |
| 6,622,726 B1 | 9/2003 | Du |
| 6,626,175 B2 | 9/2003 | Jafari et al. |
| 6,640,806 B2 | 11/2003 | Yurko |
| 6,644,310 B1 | 11/2003 | Delache et al. |
| 6,659,100 B2 | 12/2003 | O'Rourke |
| 6,662,032 B1 | 12/2003 | Gavish et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,694,978 B1 | 2/2004 | Bennarsten |
| 6,705,314 B1 | 3/2004 | O'Dea |
| 6,718,974 B1 | 4/2004 | Moberg |
| 6,722,360 B2 | 4/2004 | Doshi |
| 6,725,447 B1 | 4/2004 | Gilman et al. |
| 6,739,337 B2 | 5/2004 | Isaza |
| 6,752,151 B2 | 6/2004 | Hill |
| 6,758,216 B1 | 7/2004 | Berthon-Jones et al. |
| 6,761,167 B1 | 7/2004 | Nadjafizadeh et al. |
| 6,761,168 B1 | 7/2004 | Nadjafizadeh et al. |

(56) References Cited

U.S. PATENT DOCUMENTS

| | | |
|---|---|---|
| 6,776,159 B2 | 8/2004 | Pelerossi et al. |
| 6,782,888 B1 | 8/2004 | Friberg et al. |
| 6,786,216 B2 | 9/2004 | O'Rourke |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,848,444 B2 | 2/2005 | Smith et al. |
| 6,854,462 B2 | 2/2005 | Berthon-Jones et al. |
| 6,863,068 B2 | 3/2005 | Jamison et al. |
| 6,863,656 B2 | 3/2005 | Lurie |
| 6,866,040 B1 | 3/2005 | Bourdon |
| 6,877,511 B2 | 4/2005 | DeVries et al. |
| 6,899,103 B1 | 5/2005 | Hood et al. |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 6,986,349 B2 | 1/2006 | Lurie |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,032,589 B2 | 4/2006 | Kerechanin, II et al. |
| 7,036,504 B2 | 5/2006 | Wallace et al. |
| 7,040,318 B2 | 5/2006 | Däscher et al. |
| 7,056,334 B2 | 6/2006 | Lennox |
| 7,066,175 B2 | 6/2006 | Hamilton et al. |
| 7,066,177 B2 | 6/2006 | Pittaway et al. |
| 7,070,570 B2 | 7/2006 | Sanderson et al. |
| 7,077,131 B2 | 7/2006 | Hansen |
| 7,077,132 B2 | 7/2006 | Berthon-Jones |
| 7,080,646 B2 | 7/2006 | Wiesmann et al. |
| RE39,225 E | 8/2006 | Isaza et al. |
| 7,087,027 B2 | 8/2006 | Page |
| 7,089,932 B2 | 8/2006 | Dodds |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,104,962 B2 | 9/2006 | Lomask et al. |
| 7,117,438 B2 | 10/2006 | Wallace et al. |
| 7,121,277 B2 | 10/2006 | Ström |
| 7,122,010 B2 | 10/2006 | Böhm et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,156,095 B2 | 1/2007 | Melker et al. |
| 7,204,251 B2 | 4/2007 | Lurie |
| 7,211,049 B2 | 5/2007 | Bradley et al. |
| 7,219,666 B2 | 5/2007 | Friberg et al. |
| 7,246,618 B2 | 7/2007 | Habashi |
| 7,255,103 B2 | 8/2007 | Bassin |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,276,031 B2 | 10/2007 | Norman et al. |
| 7,278,962 B2 | 10/2007 | Lönneker Lammers |
| 7,290,544 B1 | 11/2007 | Särelä et al. |
| 7,296,573 B2 | 11/2007 | Estes et al. |
| 7,308,894 B2 | 12/2007 | Hickle |
| 7,311,668 B2 | 12/2007 | Lurie |
| 7,320,321 B2 | 1/2008 | Pranger et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,428,902 B2 | 9/2008 | Du et al. |
| 7,460,959 B2 | 12/2008 | Jafari |
| 7,465,275 B2 | 12/2008 | Stenqvist |
| 7,467,012 B1 | 12/2008 | Park et al. |
| 7,472,702 B2 | 1/2009 | Beck et al. |
| 7,478,634 B2 | 1/2009 | Jam |
| 7,481,222 B2 | 1/2009 | Reissmann |
| 7,487,773 B2 | 2/2009 | Li |
| 7,487,774 B2 | 2/2009 | Acker |
| 7,487,778 B2 | 2/2009 | Freitag |
| 7,527,058 B2 | 5/2009 | Wright et al. |
| RE40,814 E | 6/2009 | Van Brunt et al. |
| 7,547,285 B2 | 6/2009 | Kline |
| 7,552,731 B2 | 6/2009 | Jorczak et al. |
| 7,556,038 B2 | 7/2009 | Kirby et al. |
| 7,556,041 B2 | 7/2009 | Madsen |
| 7,562,657 B2 | 7/2009 | Blanch et al. |
| 7,574,368 B2 | 8/2009 | Pawlikowski et al. |
| 7,581,708 B2 | 9/2009 | Newkirk |
| 7,588,033 B2 | 9/2009 | Wondka |
| 7,617,824 B2 | 11/2009 | Doyle |
| 7,621,270 B2 | 11/2009 | Morris et al. |
| 7,628,151 B2 | 12/2009 | Bassin |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,682,312 B2 | 3/2010 | Lurie |
| 7,686,019 B2 | 3/2010 | Weiss et al. |
| 7,694,677 B2 | 4/2010 | Tang |
| 7,708,015 B2 | 5/2010 | Seeger et al. |
| 7,717,113 B2 | 5/2010 | Andrieux |
| 7,717,858 B2 | 5/2010 | Massad |
| 7,721,736 B2 | 5/2010 | Urias et al. |
| 7,722,546 B2 | 5/2010 | Madaus et al. |
| D618,356 S | 6/2010 | Ross |
| 7,730,884 B2 | 6/2010 | Sato et al. |
| 7,735,486 B2 | 6/2010 | Payne |
| 7,735,492 B2 | 6/2010 | Doshi et al. |
| 7,775,207 B2 | 8/2010 | Jaffe et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,810,498 B1 | 10/2010 | Patterson |
| 7,823,588 B2 | 11/2010 | Hansen |
| 7,841,347 B2 | 11/2010 | Sonnenschein et al. |
| 7,849,854 B2 | 12/2010 | DeVries et al. |
| 7,850,619 B2 | 12/2010 | Gavish et al. |
| 7,855,716 B2 | 12/2010 | McCreary et al. |
| 7,866,318 B2 | 1/2011 | Bassin |
| D632,796 S | 2/2011 | Ross et al. |
| D632,797 S | 2/2011 | Ross et al. |
| 7,886,739 B2 | 2/2011 | Soliman et al. |
| 7,891,354 B2 | 2/2011 | Farbarik |
| 7,893,560 B2 | 2/2011 | Carter |
| 7,909,034 B2 | 3/2011 | Sinderby et al. |
| D638,852 S | 5/2011 | Skidmore et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,971,589 B2 | 7/2011 | Mashak et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,308 B2 | 9/2011 | Carlson et al. |

(56) References Cited

U.S. PATENT DOCUMENTS

| | | |
|---|---|---|
| 8,021,309 B2 | 9/2011 | Zilberg |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 8,844,526 B2 * | 9/2014 | Jafari ............... A61M 16/0051 128/204.23 |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0004893 A1 | 6/2001 | Biondi et al. |
| 2002/0017301 A1 | 2/2002 | Lundin |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0117173 A1 | 8/2002 | Lynn et al. |
| 2002/0144681 A1 | 10/2002 | Cewers et al. |
| 2003/0029453 A1 | 2/2003 | Smith et al. |
| 2003/0140925 A1 | 7/2003 | Sapienza et al. |
| 2003/0168066 A1 | 9/2003 | Sallvin |
| 2003/0172929 A1 | 9/2003 | Muellner |
| 2003/0225339 A1 | 12/2003 | Orr et al. |
| 2004/0149282 A1 | 8/2004 | Hickle |
| 2004/0244804 A1 | 12/2004 | Olsen et al. |
| 2005/0034724 A1 | 2/2005 | O'Dea |
| 2005/0034727 A1 | 2/2005 | Shusterman et al. |
| 2005/0039748 A1 | 2/2005 | Andrieux |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0113668 A1 | 5/2005 | Srinivasan |
| 2005/0139212 A1 | 6/2005 | Bourdon |
| 2005/0166928 A1 | 8/2005 | Jiang |
| 2005/0247311 A1 | 11/2005 | Vacchiano et al. |
| 2005/0279358 A1 | 12/2005 | Richey, II |
| 2006/0021618 A1 | 2/2006 | Berthon-Jones et al. |
| 2006/0122662 A1 | 6/2006 | Tehrani et al. |
| 2006/0142815 A1 | 6/2006 | Tehrani et al. |
| 2006/0196507 A1 | 9/2006 | Bradley |
| 2006/0196508 A1 | 9/2006 | Chalvignac |
| 2006/0241708 A1 | 10/2006 | Boute |
| 2006/0249153 A1 | 11/2006 | DeVries et al. |
| 2006/0264762 A1 | 11/2006 | Starr |
| 2006/0272637 A1 | 12/2006 | Johnson |
| 2006/0283451 A1 | 12/2006 | Albertelli |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0056588 A1 | 3/2007 | Hayek |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0089741 A1 | 4/2007 | Bohm et al. |
| 2007/0123792 A1 | 5/2007 | Kline |
| 2007/0125377 A1 | 6/2007 | Heinonen et al. |
| 2007/0129646 A1 | 6/2007 | Heinonen et al. |
| 2007/0157931 A1 | 7/2007 | Parker et al. |
| 2007/0181122 A1 | 8/2007 | Mulier |
| 2007/0227537 A1 | 10/2007 | Bemister et al. |
| 2007/0272241 A1 | 11/2007 | Sanborn et al. |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0011296 A1 | 1/2008 | Schatzl |
| 2008/0021379 A1 | 1/2008 | Hickle |
| 2008/0033304 A1 | 2/2008 | Dalal et al. |
| 2008/0041383 A1 | 2/2008 | Matthews et al. |
| 2008/0045845 A1 | 2/2008 | Pfeiffer et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0135044 A1 | 6/2008 | Freitag et al. |
| 2008/0163872 A1 | 7/2008 | Negele et al. |
| 2008/0168990 A1 | 7/2008 | Cooke et al. |
| 2008/0178874 A1 | 7/2008 | Doshi et al. |
| 2008/0183057 A1 | 7/2008 | Taube |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0196720 A1 | 8/2008 | Kollmeyer et al. |
| 2008/0200775 A1 | 8/2008 | Lynn |
| 2008/0202525 A1 | 8/2008 | Mitton et al. |
| 2008/0202528 A1 | 8/2008 | Carter et al. |
| 2008/0208281 A1 | 8/2008 | Tehrani et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0283060 A1 | 11/2008 | Bassin |
| 2008/0295837 A1 | 12/2008 | McCormick et al. |
| 2008/0312519 A1 | 12/2008 | Maschke |
| 2008/0314385 A1 | 12/2008 | Brunner et al. |
| 2009/0007914 A1 | 1/2009 | Bateman |
| 2009/0013999 A1 | 1/2009 | Bassin |
| 2009/0020119 A1 | 1/2009 | Eger et al. |
| 2009/0038617 A1 | 2/2009 | Berthon-Jones et al. |
| 2009/0071478 A1 | 3/2009 | Kalfon |
| 2009/0090359 A1 | 4/2009 | Daviet et al. |
| 2009/0095297 A1 | 4/2009 | Hallett |
| 2009/0099621 A1 | 4/2009 | Lin et al. |
| 2009/0107982 A1 | 4/2009 | McGhin et al. |
| 2009/0114223 A1 | 5/2009 | Bonassa |
| 2009/0137919 A1 | 5/2009 | Bar-Lavie et al. |
| 2009/0139522 A1 | 6/2009 | Thomson et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0183739 A1 | 7/2009 | Wondka |
| 2009/0194109 A1 | 8/2009 | Doshi et al. |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0210032 A1 | 8/2009 | Beiski et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |

(56) References Cited

U.S. PATENT DOCUMENTS

| | | |
|---|---|---|
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250058 A1 | 10/2009 | Lastow et al. |
| 2009/0260625 A1 | 10/2009 | Wondka |
| 2009/0266360 A1 | 10/2009 | Acker et al. |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0299155 A1 | 12/2009 | Yang et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308393 A1 | 12/2009 | Luceros |
| 2009/0308394 A1 | 12/2009 | Levi |
| 2009/0308398 A1 | 12/2009 | Ferdinand et al. |
| 2009/0314297 A1 | 12/2009 | Mathews |
| 2010/0011307 A1 | 1/2010 | Desfossez et al. |
| 2010/0016694 A1 | 1/2010 | Martin et al. |
| 2010/0018531 A1 | 1/2010 | Bassin |
| 2010/0024818 A1 | 2/2010 | Stenzler et al. |
| 2010/0024820 A1 | 2/2010 | Bourdon |
| 2010/0031443 A1 | 2/2010 | Georgiev et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078018 A1 | 4/2010 | Heinonen et al. |
| 2010/0078024 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0089396 A1 | 4/2010 | Richard et al. |
| 2010/0094366 A1 | 4/2010 | McCarthy |
| 2010/0101575 A1 | 4/2010 | Fedorko et al. |
| 2010/0108066 A1 | 5/2010 | Martin et al. |
| 2010/0108070 A1 | 5/2010 | Kwok |
| 2010/0114218 A1 | 5/2010 | Heath |
| 2010/0116270 A1 | 5/2010 | Edwards et al. |
| 2010/0125227 A1 | 5/2010 | Bird |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0148458 A1 | 6/2010 | Ross et al. |
| 2010/0175695 A1 | 7/2010 | Jamison |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252046 A1 | 10/2010 | Dahlström et al. |
| 2010/0258124 A1 | 10/2010 | Madaus et al. |
| 2010/0275920 A1 | 11/2010 | Tham et al. |
| 2010/0275921 A1 | 11/2010 | Schindhelm et al. |
| 2010/0282259 A1 | 11/2010 | Figueiredo et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0307507 A1 | 12/2010 | Li et al. |
| 2010/0319691 A1 | 12/2010 | Lurie et al. |
| 2010/0326442 A1 | 12/2010 | Hamilton et al. |
| 2010/0326447 A1 | 12/2010 | Loomas et al. |
| 2010/0331877 A1 | 12/2010 | Li et al. |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0017214 A1 | 1/2011 | Tehrani |
| 2011/0023875 A1 | 2/2011 | Ledwith |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0061650 A1 | 3/2011 | Heesch |
| 2011/0073112 A1 | 3/2011 | DiBlasi et al. |
| 2011/0088697 A1 | 4/2011 | DeVries et al. |
| 2011/0092841 A1 | 4/2011 | Bassin |
| 2011/0100365 A1 | 5/2011 | Wedler et al. |
| 2011/0108041 A1 | 5/2011 | Sather et al. |
| 2011/0112424 A1 | 5/2011 | Kesselman et al. |
| 2011/0112425 A1 | 5/2011 | Muhlsteff et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209706 A1 | 9/2011 | Truschel et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |

(56) References Cited

U.S. PATENT DOCUMENTS

| | | |
|---|---|---|
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0114115 A1 | 4/2016 | Glenn et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operators and Technical Reference Manual. Series Ventilator System, Nellcor Puritan Bennett, Part No. 4-070088-00, Rev. L, Aug. 2010, pp. 1-476.

840 Operators and Technical Reference Manual. Ventilator System, Nellcor Puritan Bennett, Part No. 4-075609-00, Rev. G, Oct. 2006, pp. 1-424.

Hari, "Flow Sensor Fault Causing Ventilator Malfunction", Anaesthesia, 2005, 60, pp. 1042-2052; http://onlinelibrary.wiley.com/doi/10.1111/j.1365-2044.2005.04396.x/pdf; Accessed Jan. 16, 2015).

* cited by examiner

METHODS AND SYSTEMS FOR TRIGGERING WITH UNKNOWN INSPIRATORY FLOW

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes.

Triggering with Unknown Inspiratory Flow

This disclosure describes systems and methods for providing novel back-up ventilation that allows the patient to trigger or initiate the delivery of breath. Further, this disclosure describes systems and methods for triggering ventilation when base flow and/or inspiratory flow is unknown or indeterminable by the ventilator.

In part, this disclosure describes a method for ventilating a patient with a ventilator. The method includes:
 a) delivering a fixed base flow that is indeterminable;
 b) monitoring an exhalation flow during exhalation;
 c) monitoring accumulator pressure during exhalation;
 d) estimating a base flow based on the monitored accumulator pressure;
 e) detecting a flow deviation based on the estimated base flow and the monitored exhalation flow;
 f) comparing the flow deviation to an inspiratory trigger threshold; and
 g) triggering inspiration based on the comparison.

The disclosure further describes a ventilator system that includes: a pressure generating system, a ventilation tubing system, a first sensor, a second sensor, a base flow estimator module, and a trigger module. The pressure generating system is adapted to generate a flow of breathing gas. The pressure generating system delivers an indeterminable fixed base flow. The ventilation tubing system includes an inspiratory limb, an expiratory limb, and patient interface for connecting the pressure generating system to a patient. The pressure generating system includes an accumulator. The first sensor is operatively coupled to the accumulator and capable of generating a first output indicative of accumulator pressure. The second sensor is operatively coupled to at least one of the pressure generating system and the expiratory limb and capable of generating a second output indicative of an exhalation flow. The base flow estimator module determines an estimated base flow based on the first output. The flow deviation module determines a flow deviation based on the estimated base flow and the second output. The trigger module triggers inspiration based on a comparison of the flow deviation to an inspiratory trigger threshold.

The disclosure additionally describes a computer-readable medium having computer-executable instructions for performing a method for ventilating a patient with a ventilator. The method includes:
 a) repeatedly delivering a fixed base flow that is indeterminable;
 b) repeatedly monitoring an exhalation flow during exhalation;
 c) repeatedly monitoring accumulator pressure during exhalation;
 d) repeatedly estimating a base flow based on the monitored accumulator pressure;
 e) repeatedly detecting a flow deviation based on the estimated base flow and the monitored exhalation flow;
 f) repeatedly comparing the flow deviation to an inspiratory trigger threshold; and
 g) repeatedly triggering inspiration based on the comparison.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims.

DETAILED DESCRIPTION

Figure 1A:
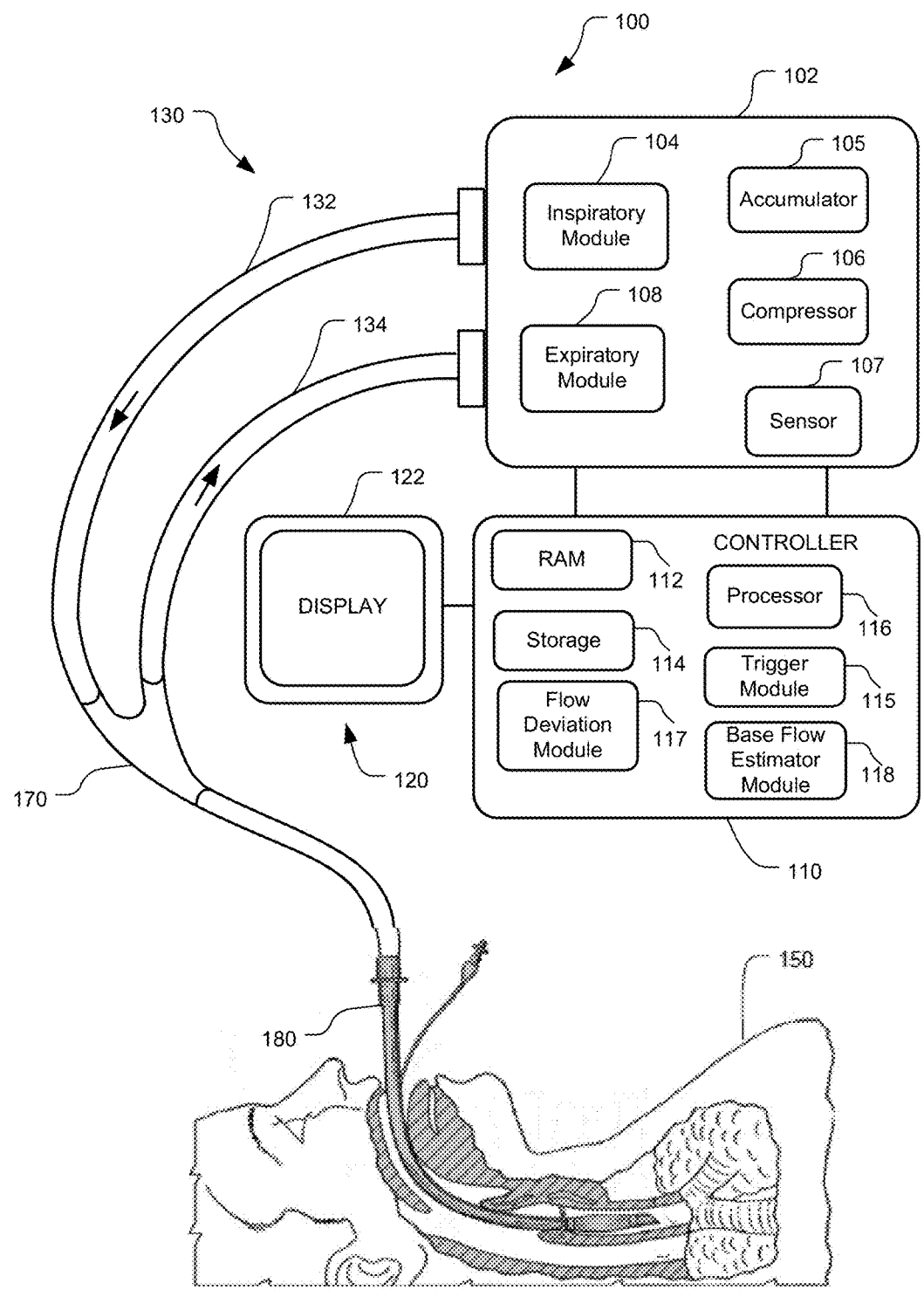
FIG. 1A illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes. Assist control modes allow a spontaneously breathing patient to trigger inspiration during ventilation.

The response performance of a medical ventilator to a patient trigger from exhalation into inhalation phase represents an important characteristic of a medical ventilator. A ventilator's trigger response impacts the patient's work of breathing and the overall patient-ventilator synchrony. The trigger response performance of a ventilator is a function of a patient's inspiratory behavior (breathing effort magnitude and timing characteristics) as well as the ventilator's gas delivery dynamics and flow control parameters (actuator response, dead bands, etc.).

In conventional flow triggering modes, a patient's inspiratory trigger is detected based on the magnitude of flow deviations generated by the patient's inspiratory effort. In a flow triggering mode, the ventilator delivers a fixed base flow during the exhalation phase. Accordingly, flow deviations are sensed by the computation of the ventilator net flow (base flow-exhausted flow) and compared against a set trigger threshold for triggering.

Base flow is the delivered flow during exhalation and consists of a desired combination of appropriate gases. A fixed base flow may be generated by a controller regulating an actuator (valve) to maintain a constant desired flow rate from a regulated pressurized gas source into the ventilator circuit. The magnitude of the flow rate generated by the delivery valve at different open positions is determined by an inspiratory flow sensor. Therefore, base flow is determined by the ventilator by measuring the amount of flow delivered to the patient via an inspiration flow sensor during exhalation.

Exhausted flow is measured during the expiratory phase of a ventilator breath while a base flow is delivered through the patient circuit. To determine the volume of gas exhaled by the patient, the net flow (total delivered flow minus total flow through exhalation module) is used for integration. That is, the delivered base flow is subtracted from the sum of the base flow and patient flow exiting through the exhalation port. The flow exiting the exhalation module during the active phase of patient exhalation is the sum of base flow delivered by the ventilator and exhaled flow from the patient lung.

In the absence of an inspiratory flow sensor or under fault conditions when an inspiratory flow sensor may not be utilized, a fixed base flow may be generated by opening the delivery valve or regulator to a fixed position and/or by controlling the input pressure, which is generated by an accumulator, to the delivery valve. However, the magnitude of the generated base flow is indeterminable, so a conventional flow triggering algorithm cannot be used to compare the net flow (base flow–exhausted flow) against the trigger threshold. Accordingly, patient initiated triggers cannot be detected and prevent the use of a spontaneous mode of ventilation.

An example of a fault condition is presented by the Back-Up Ventilation (BUV) mode under which the data measurement and acquisition subsystem on the delivery side of the ventilator is deactivated because of a malfunction. Conventional ventilators declare an alarm and terminate ventilation. However, the BUV mode allows a ventilator to continue ventilating the patient under such conditions until an appropriate substitute device is made available. However, currently, the BUV mode does not allow for spontaneously breathing patients to trigger ventilation. Therefore, the BUV mode is uncomfortable for spontaneously breathing patients.

Accordingly, the systems and methods described herein provide for a triggering mechanism when inspiration flow is unknown, which means that a fixed base flow is also indeterminable by the ventilator. As used herein, a base flow is indeterminable by the ventilator when the base flow delivered is not measurable in the inhalation limb of the ventilator tubing system. Further, the base flow may be indeterminable by the ventilator in any situation in which the ability to control the inspiratory module is questioned. The terms unreliable, unknown, and indeterminable as used herein, while having different meanings, are utilized interchangeably in this disclosure. Accordingly, the term "unreliable" encompasses the terms "indeterminable" and "unknown, the term "unknown" encompasses the terms "unreliable" and "indeterminable" and the term "unreliable" encompasses the terms "indeterminable" and "unknown." The capability of triggering without the knowledge of a flow rate for a fixed base flow allows a BUV mode to maintain comfortable patient-ventilator synchrony.

The ventilator monitors exhalation flow and accumulator pressure during exhalation. The ventilator estimates a base flow based on the accumulator pressure. The estimated base flow is substituted for the actual base flow allowing the traditional flow triggering algorithm to be utilized. For example, the ventilator is able to determine flow deviations by the computation of the ventilator net flow (base flow-exhausted) which is compared against a set trigger threshold for triggering. In some embodiments, the ventilator determines a stable portion of exhalation based on the monitored exhalation flow. In these embodiments, the ventilator may only detect for flow deviations during the stable portions of exhalations.

Figure 1B:
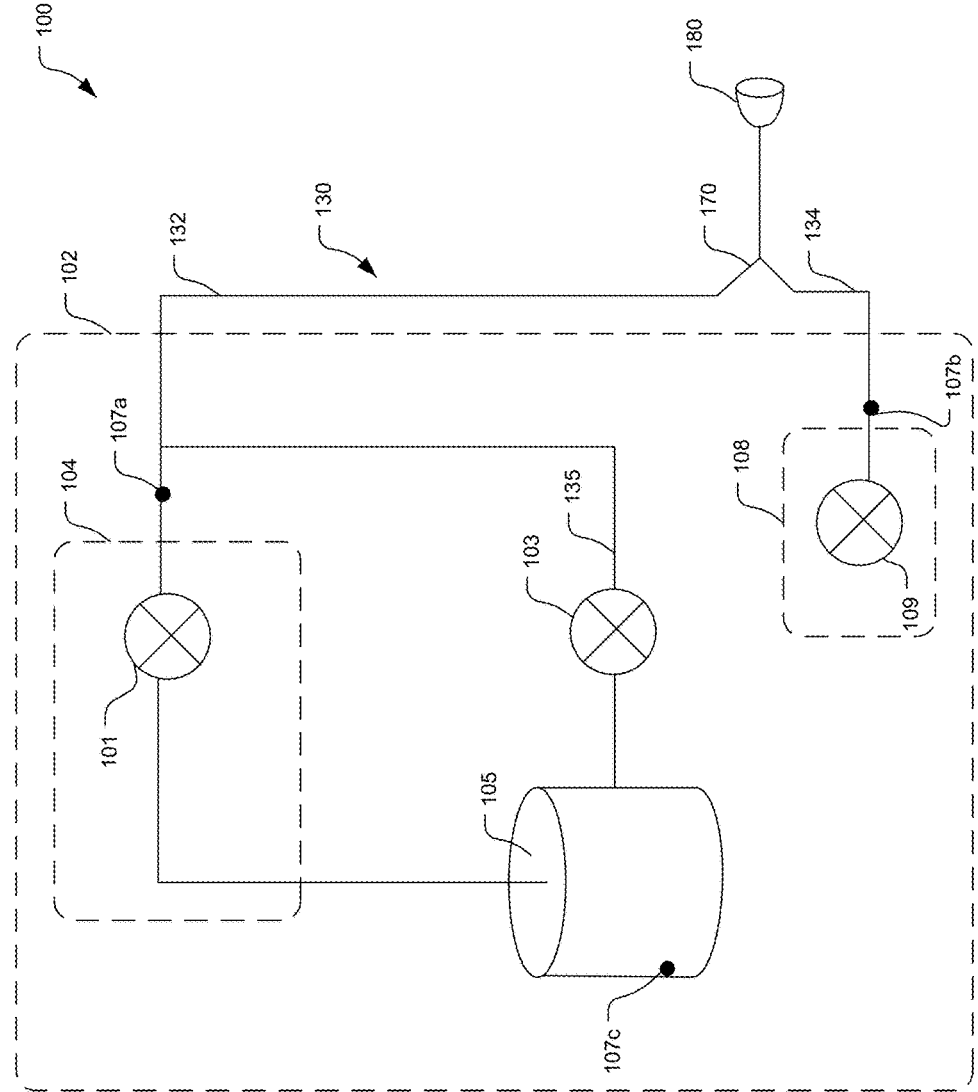
FIG. 1B illustrates an embodiment of a ventilator.

FIGS. 1A and 1B are diagrams illustrating an embodiment of an exemplary ventilator 100. The exemplary ventilator 100 illustrated in FIG. 1A is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106, accumulator 105 and/or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory valve 101 for controlling gas delivery to the patient 150 and/or gas delivery through the inspiratory limb 132. In some embodiments, inspiratory module 104 is configured to provide ventilation according to various ventilator modes, such as mandatory, spontaneous, and assist modes.

The expiratory module 108 is configured to release gases from the patient's lungs according to prescribed ventilatory settings. The expiratory module 108 is associated with and/or controls an expiratory valve 109 for releasing gases from the patient 150. Further, the expiratory module 108 and/or the inspiratory module 104 may instruct the pressure generating system 102 and/or the inspiratory module 104 to deliver a base flow during exhalation. In an alternative embodiment, the pressure generating system 102 may instruct the inspiratory module 104 to deliver a base flow during exhalation.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1A illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, trigger module 115, flow deviation module 117, base flow estimator module 118, and any other suitable components and/or modules. In one embodiment, sensors 107 generate output and send this output to pneumatic system 102, other sensors 107, expiratory module 108, inspiratory module 104, processor 116, controller 110 trigger module 115, flow deviation module 117, base flow estimator module 118, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. For example, in some embodiments, one or more sensors 107 may be located in an accumulator 105. Further, sensors 107 may be placed in any suitable internal location, such as, within the ventilatory circuitry or within components or modules of ventilator 100. For example, sensors 107 may be coupled to the inspiratory and/or expiratory modules 104, 108 for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Any sensory device useful for monitoring changes in measurable parameters during ventilatory treatment may be employed in accordance with embodiments described herein.

For example, in some embodiments, the one or more sensors 107 of the ventilator 100 include an inspiratory flow sensor 107a and an expiratory flow sensor 107b as illustrated in FIG. 1B. In one embodiment, the inspiratory flow sensor 107a is located in the inspiratory limb 132 and is controlled by the inspiratory module 104. However, the inspiratory flow sensor 107a may be located in any suitable position for monitoring inspiratory flow and may be monitored by any suitable ventilator component, such as a pressure generating system 102. In one embodiment, the expiratory flow sensor 107b is located in the expiratory limb 134 and is monitored by the expiratory module 108. However, the expiratory flow sensor 107b may be located in any suitable position for monitoring expiratory flow and may be monitored by any suitable ventilator component, such as a pressure generating system 102. In another example, a pressure sensor 107c may be located in the accumulator 105 (as illustrated in FIG. 1B) or located in a valve attached to the accumulator 105. The pressure sensor 107c may generate output indicative of the pressure within the accumulator 105. However, the pressure sensor 107c may be located in any suitable position for monitoring accumulator pressure and may be monitored by any suitable ventilator component, such as a pressure generating system 102.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships from the monitored parameters.

The pneumatic system 102 may include a variety of other components, including mixing modules, valves, tubing, accumulators 105, filters, etc. In the event that the inspiratory module 104 malfunctions, in one embodiment, the pressure generating system 102 may instruct an accumulator 105 to deliver inspiratory flow and/or base flow through a bypass limb 135 and a back-up valve 103 to the ventilation tubing system 130, as illustrated in FIG. 1B. In some embodiments, the bypass limb 135 is tubing that connects the pressure generating system 102 to the patient 150 and the expiratory limb 134 while bypassing the inspiratory module 104 and/or the inspiratory flow sensor 107a. The back-up valve 103 is a valve that controls the flow of gas through the bypass limb 135. In some embodiments, the bypass limb 135 is a portion of the ventilation tubing system 130.

In some embodiments, when the inspiratory module 104 malfunctions, so too does the inspiratory flow sensor 107a. In further embodiments, the delivered flow does not pass by and/or through the inspiratory flow sensor 107a during an inspiratory module 104 malfunction as illustrated in FIG. 1B. Accordingly, during some malfunctions, the delivered flow is not measured or is not accurately measured by an inspiratory flow sensor 107a. In other embodiments, the ventilator 100 does not contain an inspiratory flow sensor 107a.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate an estimated base flow, an exhalation flow, a restricted period, a trigger threshold, a flow deviation, and/or any other information known, received, or stored by the ventilator 100.

In some embodiments, controller 110 includes memory 112, one or more processors 116, storage 114, and/or other components of the type commonly found in command and control computing devices. Controller 110 may further include a trigger module 115, flow deviation module 117, and base flow estimator module 118, as illustrated in FIG. 1. In alternative embodiments, the trigger module 115, flow deviation module 117, and base flow estimator module 118 are located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The base flow estimator module 118 determines an estimated base flow when a fixed base flow is indeterminable by the ventilator 100. In some embodiments, the fixed base flow is indeterminable by the ventilator in any situation in which the inspiratory module and/or flow sensor are called into question. More specifically, in some embodiments, a fixed base flow is indeterminable by the ventilator 100 when at least one of the following conditions occur: an absence of an inspiratory flow sensor 107a; a malfunction of the inspiratory flow sensor 107a; a malfunction that prevents utilization of the inspiratory flow sensor 107a; an inspiratory module 104 malfunction; a malfunction that deactivates at least one of a data measurement subsystem and a data acquisition subsystem, and any other ventilator malfunction that prevents the ventilator 100 from being able to accurately and/or reliably measure inspiration flow. In some embodiments, the data measurement subsystem and the data acquisition subsystem are part of the pneumatic system 102 or controller 110. In some embodiments, during a malfunction, the ventilator 100 is capable of delivering an appropriate flow rate, such as a fixed base flow, by controlling the input pressure as generated by an accumulator 105 to a back-up valve 103, which may be held open in a fixed position. However, the amount of fixed base flow delivered cannot be determined by the ventilator 100, such as in a back-up ventilation.

The base flow estimator module 118 estimates a base flow based on output from a pressure sensor or pressure transducer 107c operatively coupled to the accumulator 105. The generated output is indicative of the accumulator pressure. Accordingly, the base flow estimator module 118 derives an estimated base flow based on accumulator pressure.

The flow deviation module 117 monitors for and determines a flow deviation based on the estimated base flow and the monitored exhalation flow. The flow deviation module 117 receives the estimated base flow from another component of the ventilator such as the base flow estimator module 118, controller 110, and/or processor 116. Further, the flow deviation module 117 receives the monitored exhalation flow from another component of the ventilator such as the base flow estimator module 118, sensor 107, controller 110, and/or processor 116. The estimated base flow is substituted for the actual base flow allowing the traditional flow triggering algorithm to be utilized. Accordingly, the flow deviation module 117 of the ventilator is able to determine flow deviations by the computation of the ventilator net flow (estimated base flow–exhausted flow). In other words, the flow deviation module 117 determines a flow deviation by subtracting exhalation flow from the estimated base flow measured during the same time period. Measurements taken during the same time period time are measurements taken within 1 second or less of each other. In some embodiments, the same time period includes measurements taken within 900 ms, 800 ms, 700 ms, 600 ms, 500 ms, 400 ms, 300 ms, 200 ms, 100 ms, 50 ms, 40 ms, 30 ms, 20 ms, 10 ms, 5 ms, or 1 ms or less of each other.

Figure 5:
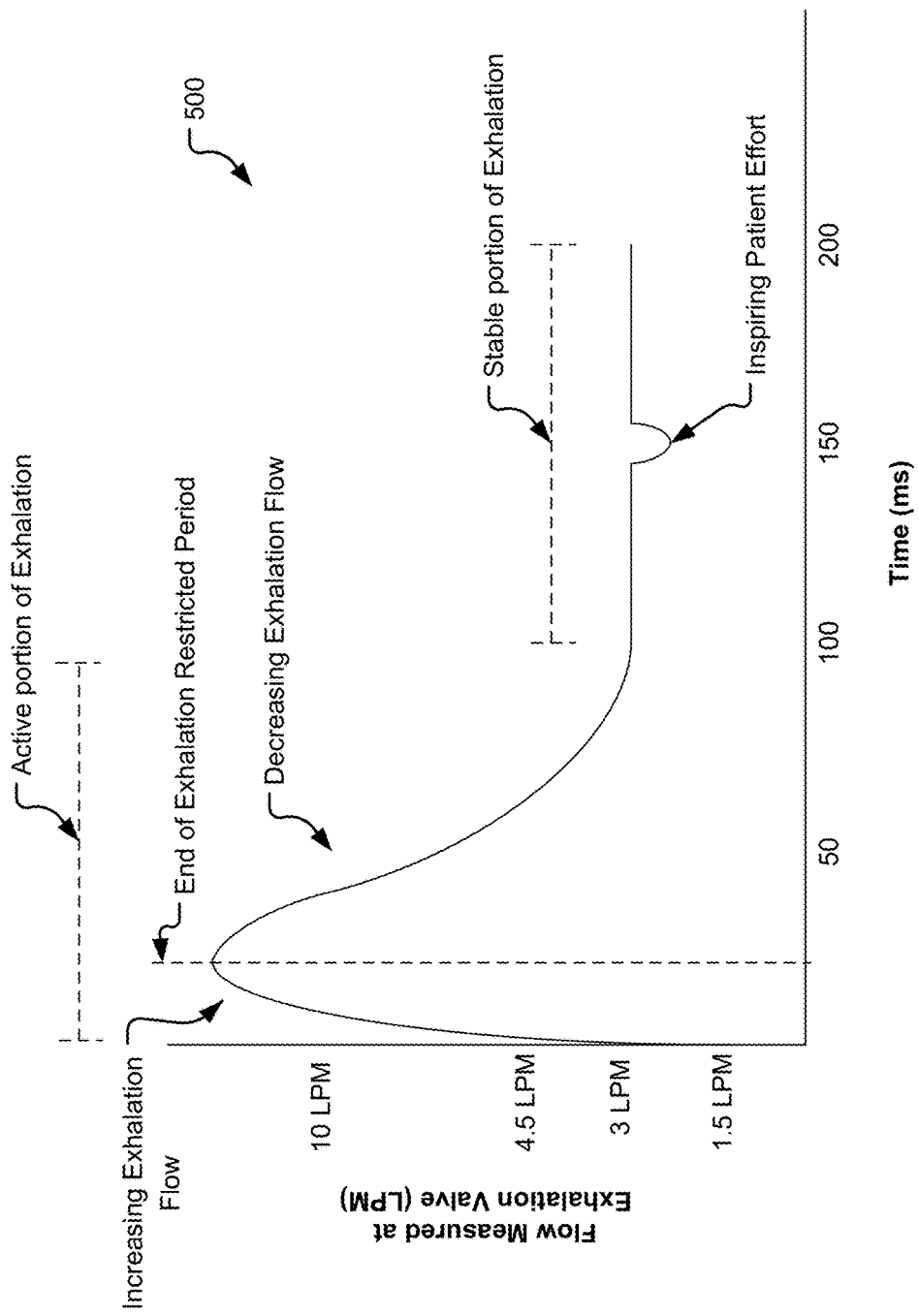
FIG. 5 illustrates an embodiment of a graph of an exhalation flow during one breath while ventilating a patient on a ventilator.

In some embodiments, the flow deviation module 117 determines a stable portion of exhalation before monitoring for flow deviations. In one embodiment, the stable portion of exhalation is the portion of exhalation when a patient 150 is contributing very little or no flow through the expiratory limb 134 and is prior to the beginning of inspiration as illustrated in FIG. 5. FIG. 5 illustrates an embodiment of a graph 500 of an exhalation flow during one breath while ventilating a patient 150 on a ventilator 100. In order to determine the stable portion of exhalation, the ventilator 100 monitors exhalation pressure and/or exhalation flow. In one embodiment, the exhaled flow and/or pressure is monitored with an expiratory flow sensor 107b. In some embodiments, the exhaled flow and/or pressure is monitored with an expiratory flow sensor 107b.

In some embodiments, the flow deviation module 117 collects multiple exhalation pressure and/or exhalation flow readings in at least two different circular buffers for a set period during exhalation after the expiration of a restricted period. The restricted period as used herein is a predetermined time period that starts at the beginning of exhalation. A patient 150 is prevented from triggering ventilation during the predetermined time period of the restricted period. For example, the restricted period may be 25 ms, 50 ms, 100 ms, and/or any other suitable time period for preventing a patient 150 from triggering inspiration.

In one embodiment, flow deviation module 117 measures exhalation flow and pressure in two 10-slot circular buffers beginning one second after the end of the restricted period. In this embodiment, to determine stability, the flow deviation module 117 may monitor the exhalation flow every computation cycle. In some embodiments, the computational cycle is every 5 ms. Next, during this embodiment, the flow deviation module 117 determines if the difference between the maximum exhalation pressure and the minimum exhalation pressure is less that 1.5 cm of $H_2O$ (($Max(P_e)-Min(P_e)$)<1.5 cm $H_2O$) and determines if the difference between maximum exhalation flow and minimum exhalation flow is less than 1.5 LPM (($Max(Q_e)-Min(Q_e)$)<1.5 LPM) during a certain interval. In this embodiment, the maximum and minimum values are calculated and compared based on the flow and pressure data saved in the 10-point buffer (pertaining to a 50 ms time period) after the initial exhalation restricted period has elapsed. Maximum and minimum values for the moving 10-point windows are tracked each computation cycle during exhalation. If the difference between the maximum exhalation pressure and the minimum exhalation pressure is less that 1.5 cm of $H_2O$ and the difference between maximum exhalation flow and minimum exhalation flow is less than 1.5 LPM, then the flow deviation module 117 determines that the patient 150 is in the stable portion of exhalation (or when active exhalation has been completed) and monitors for flow deviations. If the difference between the maximum exhalation pressure and the minimum exhalation pressure is not less than 1.5 cm of $H_2O$ and/or the difference between maximum exhalation flow and minimum exhalation flow is not less than 1.5 LPM for either computation cycle, then the flow deviation module 117 determines that the patient 150 is not in the stable portion of exhalation and does not monitor for flow deviations.

The minimum pressure and flow values of 1.5 are based on the characteristics of an exemplary ventilator. Other values and different pressure and flow levels may be used as appropriate based on the ventilator being currently utilized. Further, depending on the utilized ventilator, the flow and pressure stability thresholds may not necessarily have the same magnitude. The thresholds are selected to provide minimal respiratory activity by the patient.

In other embodiments, the flow deviation module 117 monitors the slope of the patient exhalation flow after a restricted period. If the flow deviation module 117 determines that the slope of the exhalation flow is at zero or about zero, then the flow deviation module 117 determines that the patient 150 is in the stable portion of exhalation (or when active exhalation has been completed) and monitors for flow deviations. If the flow deviation module 117 determines that the slope of the exhalation flow is not at about zero, then the flow deviation module 117 determines that the patient 150 is not in the stable portion of exhalation and does not monitor for flow deviations.

The embodiments, discussed above are merely exemplary and are not meant to be limiting. Any suitable method for determining a stable period of exhalation may be utilized by the present disclosure. In some embodiments, the flow deviation module 117 continuously updates the estimated base flow during exhalation throughout ventilation based on newly generated output from the sensor 107c operatively coupled to the accumulator 105.

Ventilators 100, depending on their mode of operation, may trigger automatically and/or in response to a detected change in a ventilator 100 and/or patient parameter. The trigger module 115 receives and/or determines one or more inspiration trigger thresholds. In some embodiments, the trigger module 115 receives an inspiration trigger threshold from operator input. In other embodiments, the trigger module 115 determines an inspiration trigger threshold based on ventilator and/or patient parameters. During exhalation, in one embodiment, the trigger module 115 monitors ventilator and/or patient parameters and compares these parameters to one or more inspiration trigger thresholds to determine if the parameters meet and/or exceed the inspiration trigger thresholds. In some embodiments, the trigger module 115 receives the ventilator and/or patient parameter form other modules of the ventilator 100, such as the pressure generating system 102, flow deviation module 117, and the base flow estimator module 118. Sensors 107 suitable for this detection may include any suitable sensing device as known by a person of skill in the art for a ventilator 100.

When a fixed base flow is indeterminable by the ventilator 100, the trigger module 115 utilizes at least one of the following trigger thresholds. In some embodiments, when a fixed base flow is indeterminable by the ventilator 100, the trigger module 115 triggers inspiration based on the first one of any of the following trigger thresholds to occur or to be exceeded.

In one embodiment, the ventilator 100 is preconfigured to deliver an inspiration after a predetermined amount of exhalation time to prevent a patient 150 from becoming under-ventilated. Accordingly, the predetermined amount of exhalation time (e.g., known as an apnea interval in some ventilators) is the trigger threshold in this embodiment. For example, the trigger module 115 will automatically trigger an inspiration after 20 seconds, 30 seconds, or 60 seconds of exhalation time. In some embodiments, the predetermined amount of time is determined by the clinician and/or ventilator 100 based on whether the patient 150 is an infant, child, adult, male, female, and/or suffering from a specific disease state.

In other embodiments, the trigger module 115 of the ventilator 100 may detect a flow-triggered event. If the ventilator 100 detects a slight drop in the base flow through the exhalation module during exhalation, this may indicate that the patient 150 is attempting to inspire. During flow triggering, the ventilator 100 is detecting a drop in base flow or a flow deviation attributable to a slight redirection of gases into the patient's lungs (in response to a slightly negative pressure gradient as discussed above). However, in some scenarios, such as during BUV, the delivered base flow is indeterminable by the ventilator 100. Accordingly, in one embodiment, a flow-triggering method when a fixed base flow is indeterminable involves the trigger module 115 comparing the flow deviation received from the flow deviation module 117 to the flow trigger threshold. As discussed above, the flow deviation determined by the flow deviation module 117 is based on the estimated base flow.

In embodiments, the trigger module 115 utilizes a change in flow rate as an inspiration trigger threshold. For example, the inspiration trigger threshold may be a change in flow rate of −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable changes in flow rate may be utilized by the trigger module 115 for triggering an inspiration.

If the trigger module 115 determines that ventilator and/or patient parameters meet and/or exceed an inspiration trigger threshold during exhalation, the trigger module 115 instructs the inspiratory module 104 to deliver an inspiration, which effectively ends the exhalation phase. If the trigger module 115 determines that ventilator and/or patient parameters do not meet and/or exceed an inspiration trigger threshold during exhalation, the trigger module 115 continues to monitor the ventilator and/or patient parameters and compare them to a trigger threshold until the ventilator and/or patient parameters meet and/or exceed a trigger threshold.

Figure 2:
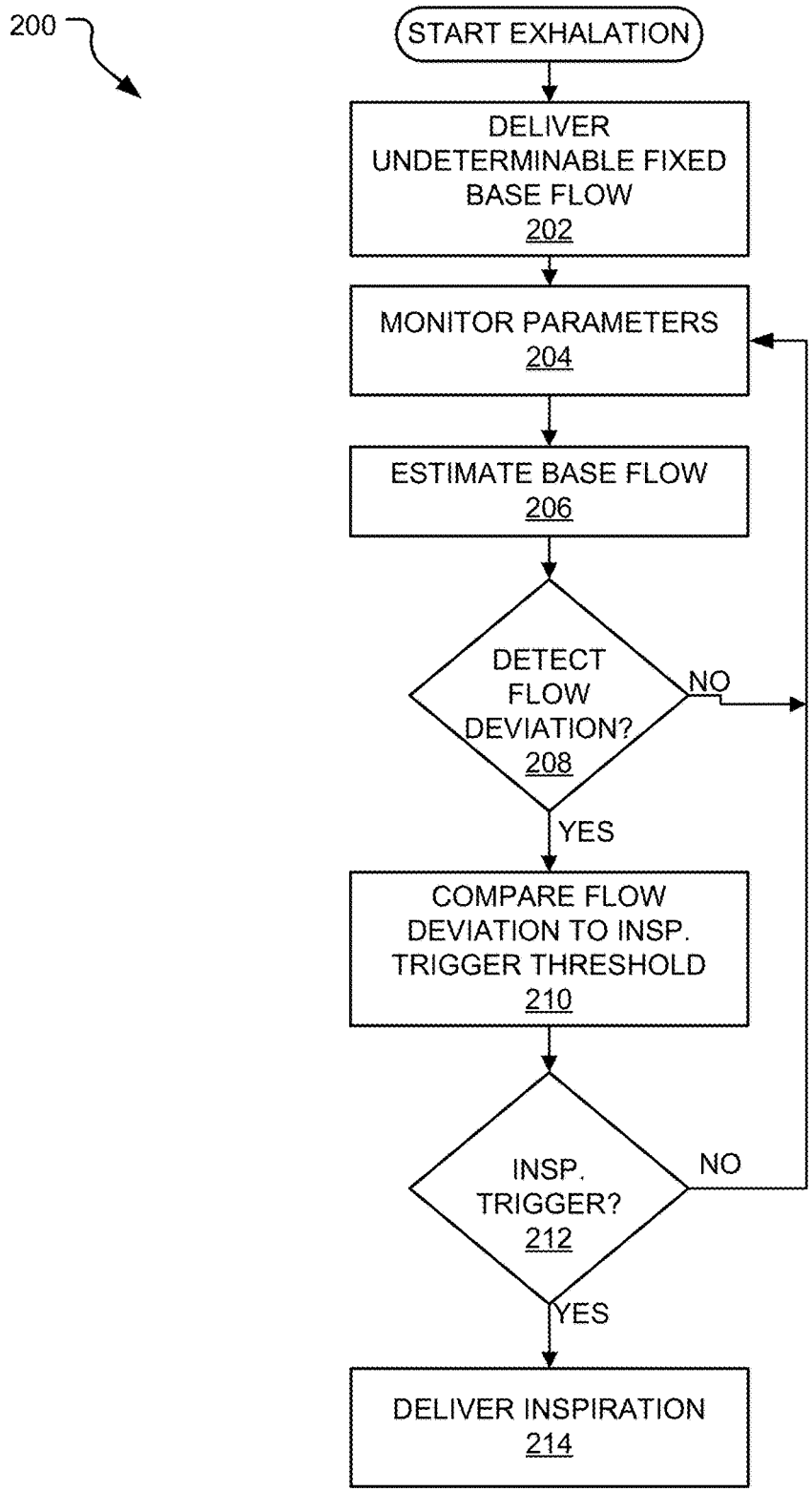
FIG. 2 illustrates an embodiment of a method for triggering inspiration during ventilation of a patient on a ventilator.

FIG. 2 illustrates an embodiment of a method 200 for triggering inspiration during ventilation of a patient on a ventilator. Method 200 begins at the start of exhalation. As illustrated, method 200 includes a deliver an indeterminable fixed base flow operation 202. During the deliver an indeterminable fixed base flow operation 202, the ventilator delivers a fixed but indeterminable base flow through the inspiratory limb. In some embodiments, a fixed base flow is indeterminable by the ventilator when at least one of the following conditions occur: an absence of an inspiratory flow sensor; a malfunction of the inspiratory flow sensor; a malfunction that prevents utilization of the inspiratory flow sensor; an inspiratory module malfunction; a malfunction that deactivates at least one of a data measurement subsystem and a data acquisition subsystem, and any other ventilator malfunction that prevents the ventilator from being able to measure inspiration flow. In some embodiments, during a malfunction, the ventilator is capable of delivering a fixed base flow by controlling the input pressure to a backup valve, which is generated by an accumulator.

Method 200 includes a monitoring operation 204. During the monitoring operation 204, the ventilator monitors ventilator and/or patient parameters. As used herein ventilator parameters include all parameter determined by the operator and/or ventilator. As used herein patient parameters include any parameter that is not determined by the ventilator and/or operator. The ventilator during the monitoring operation 204 performs at least two separate operations: an exhalation flow monitoring operation 204a; and an accumulator pressure monitoring operation 204b. These operations (204a and 204b) may be performed in any order, be performed simultaneously, or at least partially overlap in performance. The ventilator during the exhalation flow monitoring operation 204a monitors exhalation flow and/or exhalation pressure. Further, the ventilator during the accumulator pressure monitoring operation 204b monitors accumulator pressure. In some embodiments, the ventilator during the monitoring operation 204 additionally monitors exhalation time, exhalation flow (if not already monitored), exhalation pressure (if not already monitored), and/or a restricted period. Sensors suitable for this detection may include any suitable sensing device as known by a person of skill in the art for a ventilator, such as a flow sensor or a pressure sensor.

Further, method 200 includes an estimating operation 206. During the estimating operation 206 the ventilator estimates a base flow based on the monitored accumulator pressure. The ventilator derives an estimated base flow from the accumulator pressure measured by the ventilator during monitoring operation 204. In some embodiments, the monitored accumulator pressure is received from output from a pressure sensor operatively coupled to an accumulator. In some embodiments, the sensor is attached to the accumulator.

Next, method 200 includes a detecting flow deviation decision operation 208. During the detecting flow deviation decision operation 208 the ventilator monitors for a flow deviation based on the estimated base flow. The estimated base flow is substituted for the actual base flow allowing the traditional flow triggering algorithm to be utilized. Accordingly, the ventilator during the detecting flow deviation decision operation 208 determines a flow deviation by determining ventilator net flow (estimated base flow−exhausted flow). In other words, the ventilator during the detecting flow deviation decision operation 208 determines a flow deviation by subtracting exhalation flow from the estimated base flow measured during the same time period. Measurements taken during the same time period time are measurements taken within 1 second or less of each other. In some embodiments, the same time period includes measurements taken within 900 ms, 800 ms, 700 ms, 600 ms, 500 ms, 400 ms, 300 ms, 200 ms, 100 ms, 50 ms, 40 ms, 30 ms, 20 ms, 10 ms, 5 ms, or 1 ms or less of each other.

If the ventilator during the detecting flow deviation decision operation 208 determines a flow deviation, then the ventilator selects to perform comparing operation 210. If the ventilator during the detecting flow deviation decision operation 208 does not determine a flow deviation, then the ventilator selects to perform monitoring operation 204 again.

As illustrated, method 200 includes a comparing operation 210. The ventilator during the comparing operation 210 compares a detected flow deviation to an inspiration trigger threshold. In some embodiments, the inspiration trigger threshold is received from operator input. In other embodiments, the inspiration trigger threshold is based on ventilator and/or patient parameters.

In some embodiments, the inspiratory trigger threshold is at least one of the following inspiration trigger thresholds. In one embodiment, the ventilator may be preconfigured to deliver an inspiration after a predetermined amount of exhalation time to prevent a patient from becoming underventilated. Accordingly, the predetermined amount of exhalation time is the trigger threshold in this embodiment. For example, the predetermined amount of exhalation time may be 20 second, 30 seconds, or 60 seconds of exhalation time. In some embodiments, the predetermined amount of time is determined by the clinician and/or ventilator based on whether the patient is an infant, child, adult, male, female, and/or suffering from a specific disease state.

In some embodiments, a net negative change in flow rate below a delivered base flow is the inspiration trigger threshold. For example, the inspiration trigger threshold may be a change in flow rate of −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable change in flow rate below the delivered base flow may be utilized by the ventilator as an inspiration trigger threshold.

Next, method 200 includes an inspiration decision operation 212. During the inspiration decision operation 212, the ventilator determines if an inspiratory trigger is detected. The ventilator during the inspiration decision operation 212 detects an inspiratory trigger based on the comparison of the detected flow deviation to the inspiration trigger threshold as performed by the ventilator during comparing operation 210. In some embodiments, an inspiratory trigger is detected when a monitored patient and/or ventilator parameter exceeds or meets an inspiratory trigger threshold. In some embodiments, the ventilator during inspiration decision operation 212 determines a patient initiated inspiration based on the first one of a plurality of trigger thresholds to be met or exceeded.

If the ventilator during inspiration decision operation 212 determines that an inspiration threshold has been met or exceeded, the ventilator selects to perform the delivering inspiration operation 214. If the ventilator during inspiration decision operation 212 determines that an inspiration trigger threshold has not been met or exceeded, the ventilator selects to perform monitoring operation 204 again.

Method 200 includes delivering inspiration operation 214. The ventilator during delivering inspiration operation 214 delivers inspiration to the patient and ends exhalation. The inspiration provided to the patient may be determined by the ventilator and/or patient parameters. For example, the delivered inspiration may be based on a selected breath type or ventilation mode, such as BUV.

In other embodiments, method 200 includes a display operation. The ventilator during the display operation displays any suitable information for display on a ventilator. In one embodiment, the display operation displays at least one of an estimated base flow, an exhalation flow, an exhalation pressure, an accumulator pressure, a restricted period during which no inspiratory trigger is allowed, a trigger threshold, and/or any other information known, received, or stored by the ventilator.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2.

In some embodiments, the ventilator system includes: means for delivering a fixed base flow that is indeterminable; means for monitoring an exhalation flow during exhalation; means for monitoring accumulator pressure during exhalation; means for estimating a base flow based on the monitored accumulator pressure; means for detecting a flow deviation based on the estimated base flow; means for comparing the flow deviation to an inspiratory trigger threshold; and means for triggering inspiration based on the comparison.

Figure 3:
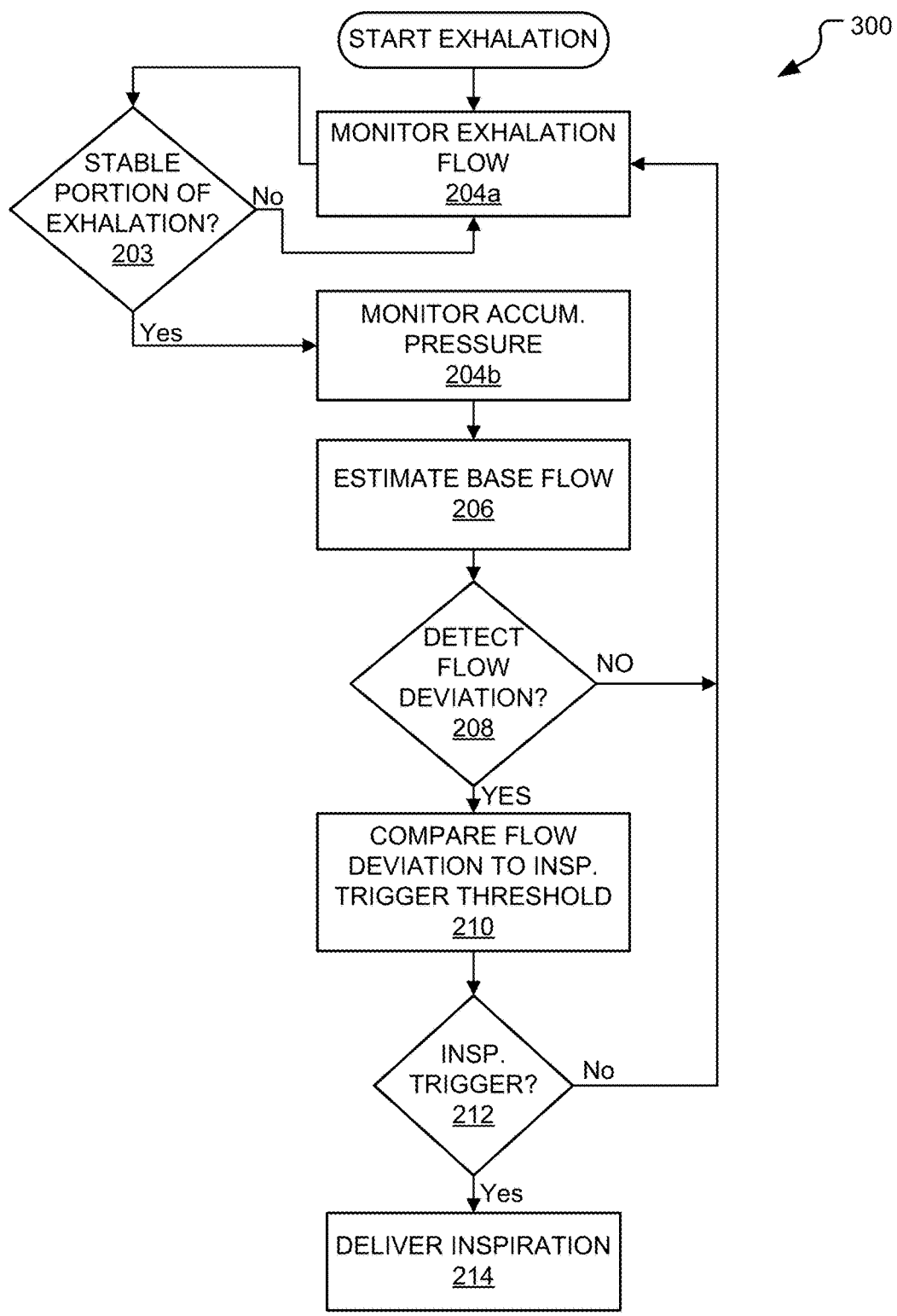
FIG. 3 illustrates an embodiment of a method for triggering inspiration during ventilation of a patient on a ventilator.
Figure 4:
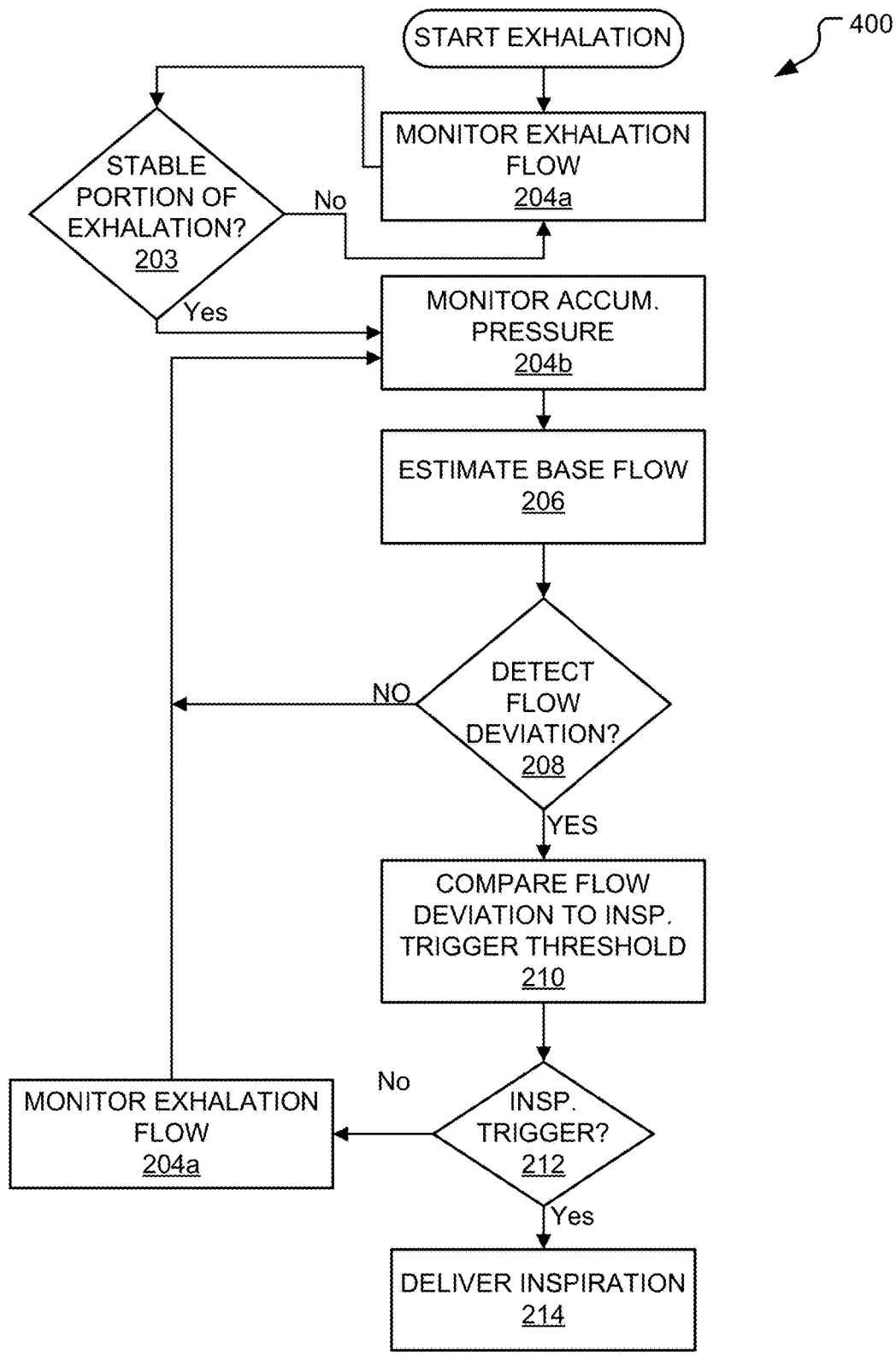
FIG. 4 illustrates an embodiment of a method for triggering inspiration during ventilation of a patient on a ventilator.

FIGS. 3 and 4 illustrate alternative embodiments of a method 300 and 400 for triggering inspiration during ventilation of a patient on a ventilator. Methods 300 and 400 provide a method for triggering inspiration when a delivered base flow is indeterminable by the ventilator. However, methods 300 and 400 require a stable portion decision operation 203 in addition to the operations disclosed in method 200.

Methods 300 and 400 begin at the start of exhalation just like method 200. As illustrated in FIGS. 3 and 4, methods 300 and 400 include an exhalation flow monitoring operation 202a. The ventilator during the exhalation flow monitoring operation 202a monitors exhalation flow and/or exhalation pressure. The ventilator does not monitor the exhalation flow and exhalation pressure until after the restricted period during which no inspiratory triggers are allowed. The ventilator may utilize any suitable sensors or measuring devices for determining the exhalation flow and exhalation pressure, such as an exhalation flow sensor and/or an exhalation pressure sensor.

Next, methods 300 and 400 include a stable portion decision operation 203. During the stable portion decision operation 203, the ventilator determines if the patient is in the stable portion of exhalation. In one embodiment, the stable portion of exhalation is the portion of exhalation when a patient is contributing very little or no flow through the patient circuit and is prior to the beginning of inspiration as illustrated in FIG. 5.

In order to determine the stable portion of exhalation, the ventilator utilizes the monitored exhalation pressure and exhalation flow. In some embodiments, the stable portion of exhalation is a time during exhalation when a slope of patient exhalation flow is about zero after a restricted period. In other embodiments, the ventilator determines if the difference between the maximum exhalation pressure and the minimum exhalation pressure is less that 1.5 cm of $H_2O$ (($Max(P_e)-Min(P_e)$)<1.5 cm $H_2O$) and determines if the difference between maximum exhalation flow and minimum exhalation flow is less than 1.5 LPM (($Max(Q_e)-Min(Q_e)$) <1.5 LPM) for a defined interval during exhalation. If the difference between the maximum exhalation pressure and the minimum exhalation pressure is less that 1.5 cm of $H_2O$ and the difference between maximum exhalation flow and minimum exhalation flow is less than 1.5 LPM for a defined interval, then the ventilator determines that the patient is in the stable portion of exhalation. If the difference between the maximum exhalation pressure and the minimum exhalation pressure is not less than 1.5 cm of $H_2O$ and/or the difference between maximum exhalation flow and minimum exhalation flow is not less than 1.5 LPM for either computation cycle, then the ventilator determines that the patient is not in the stable portion of exhalation.

The embodiments, discussed above are merely exemplary and are not meant to be limiting. Any suitable method for determining a stable period of exhalation may be utilized by the present disclosure.

If the ventilator during stable portion decision operation 203 determines that the patient has entered the stable portion of exhalation, the ventilator selects to perform the accumulator pressure monitoring operation 204b. If the ventilator during stable portion decision operation 203 determines that the patient has not entered the stable portion of exhalation, the ventilator selects to perform the exhalation flow monitoring operation 204a.

As illustrated, methods 300 and 400 also include the estimating operation 206. The estimating operation 206 is disclosed and described above in method 200.

Next, method 300 includes a detecting flow deviation decision operation 208. The detecting flow deviation decision operation 208 is disclosed and described above in method 200, except that if the ventilator during the detecting flow deviation decision operation 208 during method 300 does not determine a flow deviation, then the ventilator selects to perform, specifically, the exhalation flow monitoring operation 204a. Similarly to method 200, if the ventilator during the detecting flow deviation decision operation 208 during method 300 determines a flow deviation, then, just like in method 200, the ventilator selects to perform comparing operation 210.

Further, method 400 includes a detecting flow deviation decision operation 208. The detecting flow deviation decision operation 208 is disclosed and described above in method 200, except that if the ventilator during the detecting flow deviation decision operation 208 during method 400 does not determine a flow deviation, then the ventilator selects to perform, specifically, the exhalation flow monitoring operation 204a as illustrated in FIG. 4. However, the ventilator during method 400 after performing the exhalation flow monitoring operation 204a performs the accumulator pressure monitoring operation 204b instead of the stable portion decision operation 203 as performed in method 300. Similarly to method 200, if the ventilator during detecting flow deviation decision operation 208 during method 400 determines a flow deviation, then, just like in method 200, the ventilator selects to perform comparing operation 210.

Therefore, during method 300 if a flow deviation is not detected by the ventilator, the ventilator rechecks to confirm if the patient is in a stable portion of exhalation (or re-performs the stable portion decision operation 203) as illustrated in FIG. 3. In contrast, during method 400 if a flow deviation is not detected by the ventilator, the ventilator does not recheck to confirm that the patient is still in a stable portion of exhalation (or does not re-perform the stable portion decision operation 203) as illustrated in FIG. 4.

As illustrated, methods 300 and 400 also include the comparing operation 210. The comparing operation 210 is disclosed and described above in method 200.

Next, method 300 includes an inspiration decision operation 212. The inspiration decision operation 212 is disclosed and described above in method 200, except that if the ventilator during the inspiration decision operation 212 during method 300 determines that an inspiration trigger threshold has not been met or exceeded, the ventilator selects to perform, specifically, the exhalation flow monitoring operation 204a as illustrated in FIG. 3. Similarly to method 200, if the ventilator during inspiration decision operation 212 during method 300 determines that an inspiration threshold has been met or exceeded, the ventilator selects to perform the delivering inspiration operation 214.

Further, method 400 includes an inspiration decision operation 212. The inspiration decision operation 212 is disclosed and described above in method 200, except that if the ventilator during the inspiration decision operation 212 during method 400 determines that an inspiration trigger threshold has not been met or exceeded, the ventilator selects to perform, specifically, the exhalation flow monitoring operation 204a as illustrated in FIG. 4. However, the ventilator during method 400 after performing the exhalation flow monitoring operation 204a performs the accumulator pressure monitoring operation 204b instead of the stable portion decision operation 203 as performed in method 300. Similarly to method 200, if the ventilator during inspiration decision operation 212 during method 400 determines that an inspiration threshold has been met or exceeded, the ventilator selects to perform the delivering inspiration operation 214.

Therefore, during method 300 if an inspiration trigger is not detected by the ventilator, the ventilator rechecks to confirm if the patient is in a stable portion of exhalation (or re-performs the stable portion decision operation 203) as illustrated in FIG. 3. In contrast, during method 400 if an inspiration trigger is not detected by the ventilator, the ventilator does not recheck to confirm that the patient is still in a stable portion of exhalation (or does not re-perform the stable portion decision operation 203) as illustrated in FIG. 4.

As illustrated, methods 300 and 400 also include the delivering inspiration operation 214. The delivering inspiration operation 214 is disclosed and described above in method 200.

In other embodiments, a microprocessor-based ventilator that accesses a computer-readable medium having computer-executable instructions for performing the method of ventilating a patient with a ventilator is disclosed. This method includes repeatedly performing the steps disclosed in methods 300 or 400 above and/or as illustrated in FIGS. 3 and 4.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator, comprising:
    delivering a fixed base flow that is indeterminable with the ventilator;
    monitoring an exhalation flow during exhalation based on data from an expiratory flow sensor;
    monitoring accumulator pressure during exhalation based on data from an accumulator pressure sensor;
    estimating a base flow during exhalation based on the data from the accumulator pressure sensor with a controller;
    detecting a flow deviation based on the estimated base flow and the monitored exhalation flow with the controller;
    comparing the flow deviation to an inspiratory trigger threshold by the controller; and
    triggering inspiration with the ventilator based on the comparison by the controller.

2. The method of claim 1, wherein the fixed base flow is indeterminable because of at least one of the following conditions:
    an absence of an inspiratory flow sensor;
    a malfunction of the inspiratory flow sensor;
    a malfunction that prevents utilization of the inspiratory flow sensor;
    an inspiratory module malfunction; and
    a malfunction that deactivates at least one of a data measurement subsystem and a data acquisition subsystem.

3. The method of claim 1, further comprising:
    determining a stable portion of exhalation based at least on the monitored exhalation flow, wherein the flow deviation must be detected during the stable portion of exhalation.

4. The method of claim 3, wherein the stable portion of exhalation is a time during exhalation when a slope of patient exhalation flow is about zero after a restricted period.

5. The method of claim 3, wherein the stable portion of exhalation occurs when $(Max(P_e)-Min(P_e))<1.5$ cm $H_2O$) and $(Max(Q_e)-Min(Q_e))<1.5$ LPM) for each computation cycle, wherein $Max(P_e)$ is maximum exhalation pressure,
wherein $Min(P_e)$ is minimum exhalation pressure,
wherein $Max(Q_e)$ is maximum exhalation flow, and
wherein $Min(Q_e)$ is minimum exhalation flow.

6. The method of claim 1, wherein the inspiratory trigger threshold is a change in flow rate.

7. The method of claim 6, wherein the change is at least 5 LPM.

8. The method of claim 1, wherein the flow deviation is the monitored exhalation flow subtracted from the estimated base flow each measured at a same time period.

9. The method of claim 1, wherein the comparison shows that the flow deviation is greater than the inspiratory trigger threshold.

10. A non-transitory computer-readable medium having computer-executable instructions for performing a method of ventilating a patient with a ventilator, the method comprising:

repeatedly delivering a fixed base flow that is indeterminable with a ventilator;
repeatedly monitoring accumulator pressure during exhalation based on data from an accumulator sensor;
repeatedly estimating a base flow during exhalation based on the data with a controller;
repeatedly detecting a flow deviation based on the estimated base flow with a controller;
repeatedly comparing the flow deviation to an inspiratory trigger threshold by the controller; and
repeatedly triggering inspiration with the ventilator based on the comparison by the controller.

* * * * *